(12) United States Patent
Wu et al.

(10) Patent No.: US 8,182,427 B2
(45) Date of Patent: May 22, 2012

(54) ULTRASONIC IMAGING APPARATUS AND ULTRASONIC IMAGING METHOD

(75) Inventors: Fanggang Wu, Wuxi (CN); Huiren Chen, Wuxi (CN); Shui Xi, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 453 days.

(21) Appl. No.: 12/274,934

(22) Filed: Nov. 20, 2008

(65) Prior Publication Data

US 2009/0137904 A1    May 28, 2009

(30) Foreign Application Priority Data

Nov. 22, 2007   (CN) .......................... 2007 1 0305161

(51) Int. Cl.
*A61B 8/00* (2006.01)
(52) U.S. Cl. .................. 600/447; 600/443; 382/294
(58) Field of Classification Search .................. 600/407, 600/440, 441, 443, 444, 447, 455, 459, 472; 382/294–295, 302; 73/624–626
See application file for complete search history.

(56) References Cited

U.S. PATENT DOCUMENTS

| | | | |
|---|---|---|---|
| 4,852,577 A | | 8/1989 | Smith et al. |
| 5,261,408 A | * | 11/1993 | Maslak et al. ................. 600/447 |
| 5,529,070 A | | 6/1996 | Augustine et al. |
| 5,588,435 A | * | 12/1996 | Weng et al. .................... 600/443 |
| 5,899,861 A | * | 5/1999 | Friemel et al. ................ 600/443 |
| 6,102,865 A | | 8/2000 | Hossack et al. |
| 6,132,376 A | | 10/2000 | Hossack et al. |
| 6,201,900 B1 | | 3/2001 | Hossack et al. |
| 6,222,948 B1 | * | 4/2001 | Hossack et al. ............... 382/294 |
| 6,360,027 B1 | | 3/2002 | Hossack et al. |
| 6,685,643 B1 | | 2/2004 | Waldinger et al. |
| 6,733,458 B1 | | 5/2004 | Steins et al. |

FOREIGN PATENT DOCUMENTS

JP    2006-095151    4/2006

* cited by examiner

*Primary Examiner* — Brian Casler
*Assistant Examiner* — Michael N Fisher
(74) *Attorney, Agent, or Firm* — Armstrong Teasdale LLP

(57) ABSTRACT

An ultrasonic imaging apparatus captures a plurality of B-mode images of a same cross section respectively by a plurality of linear scans with different directional ultrasonic beams and creates and displays a compound image from the plurality of B-mode images. The ultrasonic imaging apparatus includes a device for capturing an image to capture a plurality of B-mode images respectively by a linear scan with an ultrasonic beam steered to a reference direction and a linear scan or scans with an ultrasonic beam or beams steered to one or more directions different from the reference direction, a device for creating an image to create a compound image using the plurality of B-mode images, and a display device to display the compound image.

18 Claims, 9 Drawing Sheets

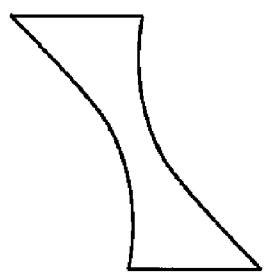
a
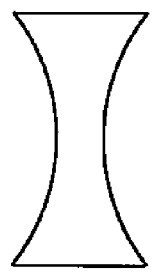
b
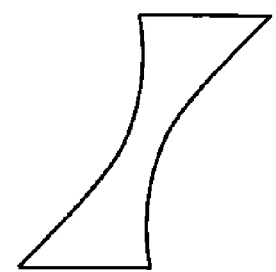
c
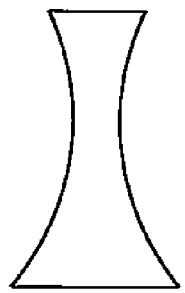
d
FIG. 9

ULTRASONIC IMAGING APPARATUS AND ULTRASONIC IMAGING METHOD

CROSS REFERENCE TO RELATED APPLICATIONS

This application claims the benefit of Chinese Patent Application No. 200710305161.1 filed Nov. 22, 2007, which is hereby incorporated by reference in its entirety.

BACKGROUND OF THE INVENTION

The subject matter disclosed herein relates to an ultrasonic imaging apparatus and, particularly, relates to an ultrasonic imaging apparatus that captures a plurality of B-mode images of a same cross section respectively by a plurality of linear scans with different directional ultrasonic beams and creates and displays a compound image from these B-mode images.

An ultrasonic imaging apparatus scans a range to be imaged with an ultrasonic beam, generates a B-mode image from echo signals received, and displays the image. Some ultrasonic imaging apparatus captures a plurality of B-mode images of a same cross section by a plurality of linear scans with different directional ultrasonic beams respectively and creates and displays a compound image from these B-mode images (refer to, e.g., Japanese Published Unexamined Patent Application No. 2006-095151).

The ultrasonic imaging apparatus is also used as support equipment when an invasive treatment on a living body is performed. In particular, for example, when a needle is inserted into the body toward a target within the body, an image in which the target and the needle are tracked within a same FOV (Filed of View) is captured and displayed and this image is used as guidance or navigation for needle insertion (refer to, e.g., U.S. Pat. No. 6,733,458).

For images used for guidance or navigation for invasive treatment, a proper FOV (Field of View) and a high image quality are required. A proper FOV is necessary for bringing an invasive medical device such as a needle entirely into view and a high image quality is necessary for visualizing clear images of both the target and the invasive medical device.

A convex scan or a virtual convex scan is performed to obtain an FOV suitable for invasive treatment. In these scans, however, because the density of acoustic lines decreases in a far field, a decrease in the image quality is inevitable.

BRIEF DESCRIPTION OF THE INVENTION

It is desirable that the problem described previously is solved.

A first aspect of the invention resides in an ultrasonic imaging apparatus that captures a plurality of B-mode images of a same cross section respectively by a plurality of linear scans with different directional ultrasonic beams and creates and displays a compound image from the plurality of B-mode images, the ultrasonic imaging apparatus characterized by including a device for capturing an image to capture a plurality of B-mode images respectively by a linear scan with an ultrasonic beam steered to a reference direction and a linear scan or scans with an ultrasonic beam or beams steered to one or more directions different from the reference direction; a device for creating an image to create a compound image using the plurality of B-mode images; and a display device to display the compound image.

A second aspect of the invention resides in the ultrasonic imaging apparatus according to the first aspect, characterized in that the reference direction is angled to the right.

A third aspect of the invention resides in the ultrasonic imaging apparatus according to the first aspect, characterized in that the reference direction is angled to the left.

A fourth aspect of the invention resides in the ultrasonic imaging apparatus according to the first aspect, characterized in that the FOV of the compound image coincides with the FOV of a B-mode image captured by a linear scan with an ultrasonic beam steered to the reference direction.

A fifth aspect of the invention resides in an ultrasonic imaging apparatus that captures a plurality of B-mode images of a same cross section by a plurality of linear scans with different directional ultrasonic beams respectively and creates and displays a compound image from the plurality of B-mode images, the ultrasonic imaging apparatus characterized by including a device for capturing a right oblique image to capture a plurality of B-mode images respectively by a linear scan with an ultrasonic beam oriented at a reference direction that is angled to the right and a linear scan or scans with an ultrasonic beam or beams steered to one or more directions different from the reference direction; a device for capturing an image at a right angle to the front to capture a plurality of B-mode images respectively by a linear scan with an ultrasonic beam oriented at a reference direction that is square to the front and a linear scan or scans with an ultrasonic beam or beams steered to one or more directions different from the reference direction; a device for capturing a left oblique image to capture a plurality of B-mode images respectively by a linear scan with an ultrasonic beam oriented at a reference direction that is angled to the left and a linear scan or scans with an ultrasonic beam or beams steered to one or more directions different from the reference direction; a device for creating a first compound image to create a first compound image using the plurality of B-mode images captured by the device for capturing a right oblique image; a device for creating a second compound image to create a second compound image using the plurality of B-mode images captured by the device for capturing an image at a right angle to the front; a device for creating a third compound image to create a third compound image using the plurality of B-mode images captured by the device for capturing a left oblique image; a device for creating an expanded image to create an expanded compound image by combining any two or all of the first compound image, the second compound image, and the third compound image; and a display device to display the expanded compound image.

A sixth aspect of the invention resides in the ultrasonic imaging apparatus according to the fifth aspect, characterized in that the FOV of the first compound image coincides with the FOV of a B-mode image captured by a linear scan with an ultrasonic beam oriented at the reference direction angled to the right; the FOV of the second compound image coincides with the FOV of a B-mode image captured by a linear scan with an ultrasonic beam oriented at the reference direction square to the front; the FOV of the third compound image coincides with the FOV of a B-mode image captured by a linear scan with an ultrasonic beam oriented at the reference direction angled to the left; and the FOV of the expanded compound image coincides with an FOV composed of any two or all of the FOV of the first compound image, the FOV of the second compound image, and the FOV of the third compound image.

A seventh aspect of the invention resides in the ultrasonic imaging apparatus according to the first aspect of the fifth aspect, characterized in that the reference direction is variably angled.

An eighth aspect of the invention resides in the ultrasonic imaging apparatus according to the first aspect of the fifth aspect, characterized in that the one or more directions are two directions.

A ninth aspect of the invention resides in the ultrasonic imaging apparatus according to the eighth aspect, characterized in that the two directions are one direction steered rightward and the other direction steered leftward relative to the reference direction.

A tenth aspect of the invention resides in the ultrasonic imaging apparatus according to the fourth aspect or the sixth aspect, characterized in that the display device displays an icon for the FOV.

An eleventh aspect of the invention resides in an ultrasonic imaging method that captures a plurality of B-mode images of a same cross section respectively by a plurality of linear scans with different directional ultrasonic beams and creates and displays a compound image from the plurality of B-mode images, the ultrasonic imaging method characterized by including capturing a plurality of B-mode images respectively by a linear scan with an ultrasonic beam steered to a reference direction and a linear scan or scans with an ultrasonic beam or beams steered to one or more directions different from the reference direction; creating a compound image using the plurality of B-mode images; and displaying the compound image.

A twelfth aspect of the invention resides in the ultrasonic imaging method according to the eleventh aspect, characterized in that the reference direction is angled to the right.

A thirteenth aspect of the invention resides in the ultrasonic imaging method according to the eleventh aspect, characterized in that the reference direction is angled to the left.

A fourteenth aspect of the invention resides in the ultrasonic imaging method according to the eleventh aspect, characterized in that the FOV of the compound image coincides with the FOV of a B-mode image captured by a linear scan with an ultrasonic beam steered to the reference direction.

A fifteenth aspect of the invention resides in an ultrasonic imaging method that captures a plurality of B-mode images of a same cross section respectively by a plurality of linear scans with different directional ultrasonic beams and creates and displays a compound image from the plurality of B-mode images, the ultrasonic imaging method characterized by including capturing a plurality of B-mode images respectively by a linear scan with an ultrasonic beam oriented at a reference direction that is angled to the right and a linear scan or scans with an ultrasonic beam or beams steered to one or more directions different from the reference direction; capturing a plurality of B-mode images respectively by a linear scan with an ultrasonic beam oriented at a reference direction that is square to the front and a linear scan or scans with an ultrasonic beam or beams steered to one or more directions different from the reference direction; capturing a plurality of B-mode images respectively by a linear scan with an ultrasonic beam oriented at a reference direction that is angled to the left and a linear scan or scans with an ultrasonic beam or beams steered to one or more directions different from the reference direction; creating a first compound image using the plurality of B-mode images captured, angled to the right; creating a second compound image using the plurality of B-mode images captured, square to the front; creating a third compound image using the plurality of B-mode images captured, angled to the left; creating an expanded compound image by combining any two or all of the first compound image, the second compound image, and the third compound image; and displaying the expanded compound image.

A sixteenth aspect of the invention resides in the ultrasonic imaging method according to the fifteenth aspect, characterized in that the FOV of the first compound image coincides with the FOV of a B-mode image captured by a linear scan with an ultrasonic beam oriented at the reference direction angled to the right; the FOV of the second compound image coincides with the FOV of a B-mode image captured by a linear scan with an ultrasonic beam oriented at the reference direction square to the front; the FOV of the third compound image coincides with the FOV of a B-mode image captured by a linear scan with an ultrasonic beam oriented at the reference direction angled to the left; and the FOV of the expanded compound image coincides with an FOV composed of any two or all of the FOV of the first compound image, the FOV of the second compound image, and the FOV of the third compound image.

A seventeenth aspect of the invention resides in the ultrasonic imaging method according to the eleventh aspect or the fifteenth aspect, characterized in that the reference direction is variably angled.

An eighteenth aspect of the invention resides in the ultrasonic imaging method according to the eleventh aspect or the fifteenth aspect, characterized in that the one or more directions are two directions.

A nineteenth aspect of the invention resides in the ultrasonic imaging method according to the eighteenth aspect, characterized in that the two directions are one direction steered rightward and the other direction steered leftward relative to the reference direction.

A twentieth aspect of the invention resides in the ultrasonic imaging method according to the fourteenth aspect or the sixteenth aspect, characterized in that the display device displays an icon for the FOV.

In the first aspect, the ultrasonic imaging apparatus that captures a plurality of B-mode images of a same cross section respectively by a plurality of linear scans with different directional ultrasonic beams and creates and displays a compound image from the plurality of B-mode images includes a device for capturing an image to capture a plurality of B-mode images respectively by a linear scan with an ultrasonic beam steered to a reference direction and a linear scan or scans with an ultrasonic beam or beams steered to one or more directions different from the reference direction; a device for creating an image to create a compound image using the plurality of B-mode images; and a display device to display the compound image. Therefore, it is possible to realize an ultrasonic imaging apparatus that satisfies both requirements of a proper FOV and a high image quality.

In the second aspect, the reference direction is angled to the right; therefore, the far field of FOV can be shifted rightward.

In the third aspect, the reference direction is angled to the left; therefore, the far field of FOV can be shifted leftward.

In the fourth aspect, the FOV of the compound image coincides with the FOV of a B-mode image captured by a linear scan with an ultrasonic beam steered to the reference direction; therefore, the FOV in which the far field was shifted rightward or leftward can be obtained.

In the fifth aspect, the ultrasonic imaging apparatus that captures a plurality of B-mode images of a same cross section by a plurality of linear scans with different directional ultrasonic beams respectively and creates and displays a compound image from the plurality of B-mode images includes a device for capturing a right oblique image to capture a plurality of B-mode images respectively by a linear scan with an ultrasonic beam oriented at a reference direction that is angled to the right and a linear scan or scans with an ultrasonic beam or beams steered to one or more directions different from the reference direction; a device for capturing an image at a right angle to the front to capture a plurality of B-mode images respectively by a linear scan with an ultrasonic beam oriented at a reference direction that is square to the front and a linear scan or scans with an ultrasonic beam or beams steered to one or more directions different from the reference direction; a device for capturing a left oblique image to capture a plurality of B-mode images respectively by a linear scan with an ultrasonic beam oriented at a reference direction that is angled to the left and a linear scan or scans with an ultrasonic beam or beams steered to one or more directions different from the reference direction; a device for creating a first compound image to create a first compound image using the plurality of B-mode images captured by the device for capturing a right oblique image; a device for creating a second compound image to create a second compound image using the plurality of B-mode images captured by the device for capturing an image at a right angle to the front; a device for creating a third compound image to create a third compound image using the plurality of B-mode images captured by the device for capturing a left oblique image; a device for creating an expanded image to create an expanded compound image by combining any two or all of the first compound image, the second compound image, and the third compound image; and a display device to display the expanded compound image. Therefore, it is possible to realize an ultrasonic imaging apparatus that satisfies both requirements of a proper FOV and a high image quality.

In the sixth aspect, the FOV of the first compound image coincides with the FOV of a B-mode image captured by a linear scan with an ultrasonic beam oriented at the reference direction angled to the right; the FOV of the second compound image coincides with the FOV of a B-mode image captured by a linear scan with an ultrasonic beam oriented at the reference direction square to the front; the FOV of the third compound image coincides with the FOV of a B-mode image captured by a linear scan with an ultrasonic beam oriented at the reference direction angled to the left; and the FOV of the expanded compound image coincides with an FOV composed of any two or all of the FOV of the first compound image, the FOV of the second compound image, and the FOV of the third compound image. Therefore, a trapezoidal-shape image FOV in which the far field broadens can be obtained.

In the seventh aspect, the reference direction is variably angled; therefore, the amount of shift of the far field of FOV can be altered.

In the eighth aspect, the one or more directions are two directions; therefore, three B mode images including one oriented at the reference direction can be obtained.

In the ninth aspect, the two directions are one direction steered rightward and the other direction steered leftward relative to the reference direction; therefore, the obtained images have symmetry with regard to the reference direction.

In the tenth aspect, the display device displays an icon for the FOV; therefore, FOV shape can be recognized easily.

Further objects and advantages of the present invention will be apparent from the following description of embodiments of the invention as illustrated in the accompanying drawings.

BRIEF DESCRIPTION OF THE DRAWINGS

FIG. 9 is a diagram depicting an example of icons.

DETAILED DESCRIPTION OF THE INVENTION

In the following, various embodiments of the invention will be described in detail with reference to the drawings. It should be understood that the invention is not limited to embodiments described herein.

Figure 1:
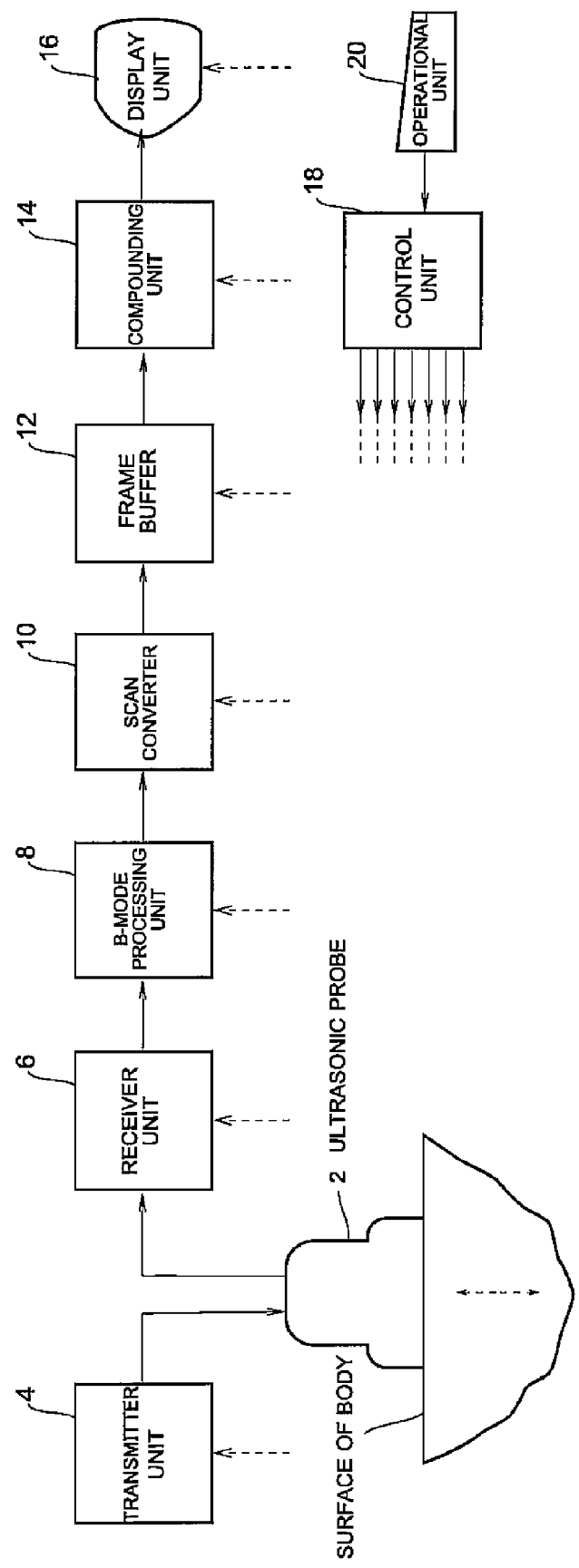
FIG. 1 is a block diagram of an ultrasonic imaging apparatus, which is an example of best mode for carrying out the invention.

A block of an exemplary ultrasonic imaging apparatus is shown in FIG. 1.

As shown in FIG. 1, the apparatus includes an ultrasonic probe 2. The ultrasonic probe 2 has an ultrasonic transducer array. In the ultrasonic transducer array, each individual ultrasonic transducer is made of piezoelectric material such as, for example, PZT (lead (Pb) zirconate (Zr) titanate (Ti)), ceramics, etc.

The ultrasonic probe 2 is used in touch with the surface of the body. To the ultrasonic probe 2, a transmitter unit 4 and a receiver unit 6 are connected. The transmitter unit 4 outputs a signal to drive the ultrasonic probe 2, thereby causing the ultrasonic probe 2 to perform scanning with an ultrasonic beam. The receiver unit 6 performs amplification and received beam forming of a received echo signal that has been input from the ultrasonic probe 2.

Figure 2:
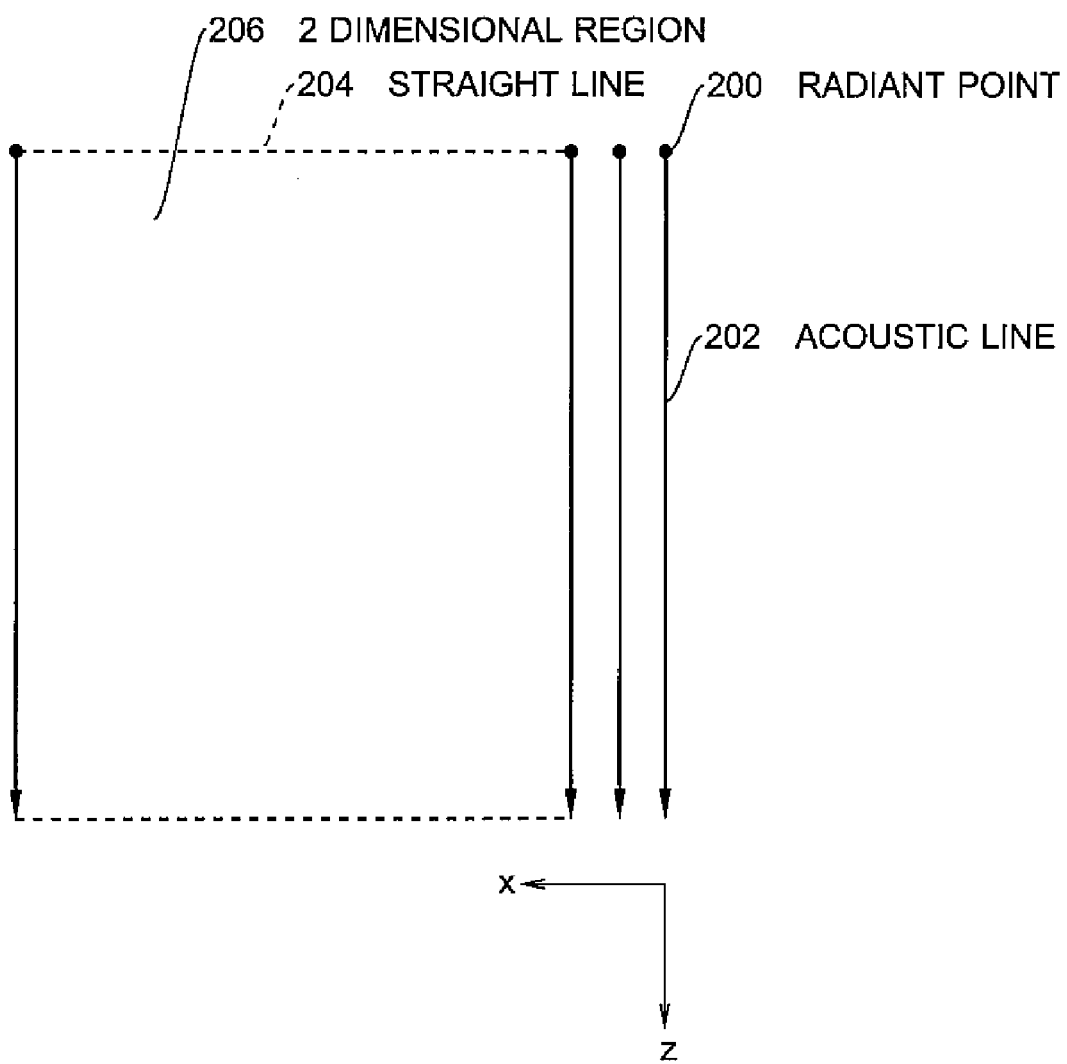
FIG. 2 is a diagram depicting a concept of a linear scan.

FIG. 2 depicts a concept of scanning with an ultrasonic beam. As depicted here, scanning is parallel shifting of an acoustic line 202 that extends in the z direction from a radiant point 200 along a straight line 204, so that the acoustic line sweeps over a rectangular two-dimensional region 206 in the x direction. Thereby, a linear scan is performed.

The acoustic line 202 corresponds to a central axis of an ultrasonic beam. The sweep of the acoustic line 202 is performed by parallel shifting of an aperture of an ultrasonic beam in the sweep direction. Movement of the aperture is performed by successively changing a combination of a plurality of ultrasonic transducers involved in forming an ultrasonic beam.

Figure 3:
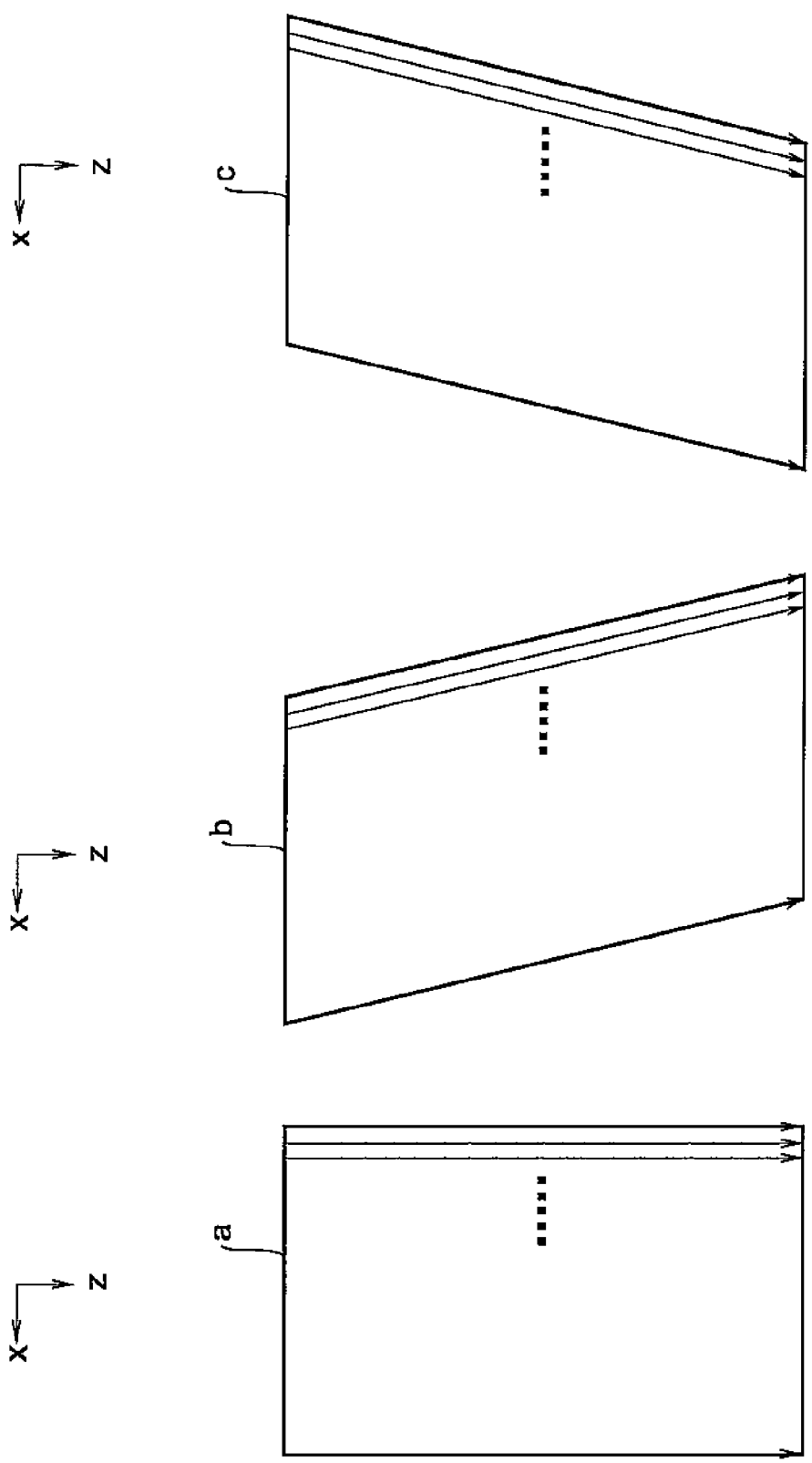
FIG. 3 is a diagram depicting a concept of a compound scan.

The apparatus carries out a compound scan utilizing linear scans. FIG. 3 depicts the concept of a compound scan. As shown in FIG. 3, a compound scan is performed as a scan consisting of, for example, a set of three frames. The direction of acoustic lines, or ultrasonic beams is different from one frame to another. These frames are on a same cross-section plane to be imaged.

A first frame a is scanned with acoustic lines oriented to the z direction. A second frame b is scanned with acoustic lines steered rightward with regard to the z direction. A third frame c is scanned with acoustic lines steered leftward with regard to the z direction.

The compound scan is not limited to three frames; the scan may consist of a set of two frames or a set of four frames or more. Although the following description is based on an example of a compound scan consisting of a set of three frames, the same is true for other cases.

In a linear scan, the density of acoustic lines is uniform across a frame from a near field to a far field. That is, for the frame a, the density of acoustic lines oriented in the z direction is uniform across the frame. For the frame b, the density of acoustic line steered rightward is uniform across the frame. For the frame c, the density of acoustic line steered leftward is uniform across the frame.

An output signal of the receiver unit 6 is input to a B-mode processing unit 8. The B-mode processing unit 8 detects an input signal and generates a B-mode image signal in which amplitude corresponds to a luminance value. B-mode image signals are generated, respectively, for three frames in which acoustic lines are oriented at different directions.

The B-mode image signals are input to a scan converter 10. The scan converter 10 maps scan data in a B-mode image signal that is arranged in order of acoustic lines into a lattice array in a two-dimensional space by scan conversion.

Scan converted B-mode image signals are buffered into a frame buffer 12. The B-mode image signals for three frames in which acoustic lines are oriented at different directions are buffered in the frame buffer 12.

The B-mode image signals from the frame buffer 12 are input to a compounding unit 14. The B-mode image signals input thereto are one set of the signals obtained by the compound scan. The compounding unit 14 aggregates these B-mode image signals in one set and generates a compound image signal.

Figure 4:
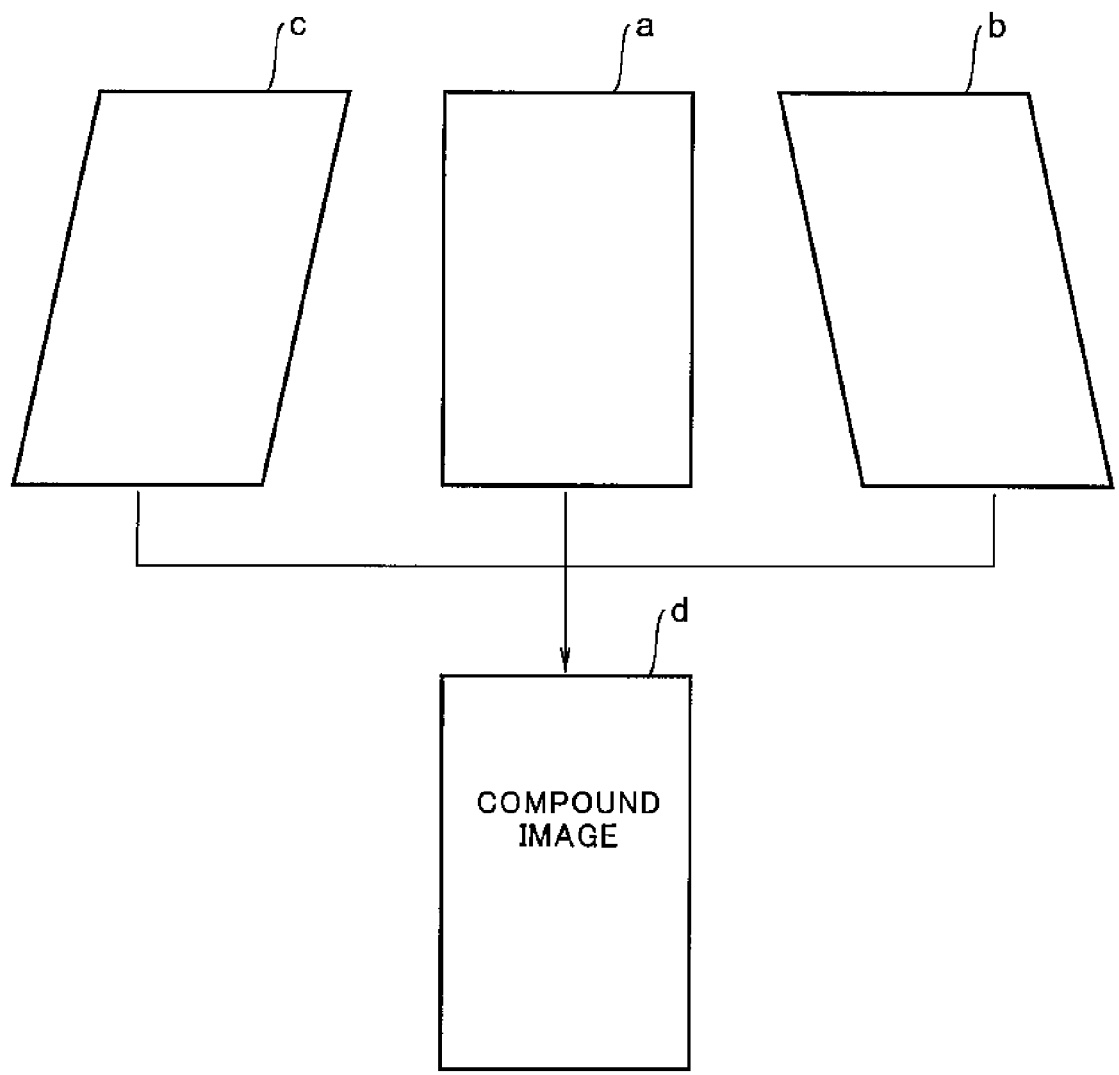
FIG. 4 is a diagram depicting a concept of creating a compound image.

FIG. 4 depicts a concept of aggregation of images. As shown in FIG. 4, a compound image d is generated by aggregating the images of three frames a, b, c. Hereinafter, aggregation of frame images will simply be referred to aggregation of frames.

In the compound image d, the images of actual echo sources are enhanced by aggregation, whereas random signal components like noise and speckle depress each other by aggregation. Consequently, the contrast resolution of the images of actual echo sources is improved and noise and speckle are reduced.

All the images of three frames a, b, c are those obtained by linear scans and, therefore, the acoustic line density is uniform across the frame from near field to far field in the compound image d as well.

The resulting compound image d is a high quality image in which the acoustic line density is uniform throughout all fields, the contrast resolution is high, and noise and speckle are small.

Such a compound image d is input from the compounding unit 14 to a display unit 16 and displayed as a visible image by the display unit 16. The display unit 16 is configured with, for example, a graphic display or the like.

The transmitter unit 4, receiver unit 6, B-mode processing unit 8, scan converter 10, frame buffer 12, compounding unit 14, and display unit 16 are controlled by a control unit 18. As the control unit 18, for example, a computer or the like is used.

To the control unit 18, a user's operational command is input via an operation unit 20. As the operation unit 20, for example, a keyboard or the like is used. A pointing device is attached to the keyboard. As the pointing device, for example, a track ball or the like is used.

An image displayed on the display unit 16 is utilized as an image for guidance or navigation when an invasive treatment on a patient is performed. To enhance convenience in such application, the apparatus is arranged such that the FOV of the compound image d can be adjusted according to the direction for an invasive medical device to take. FOV adjustment is performed by the user via the operation unit 20.

Figure 5:
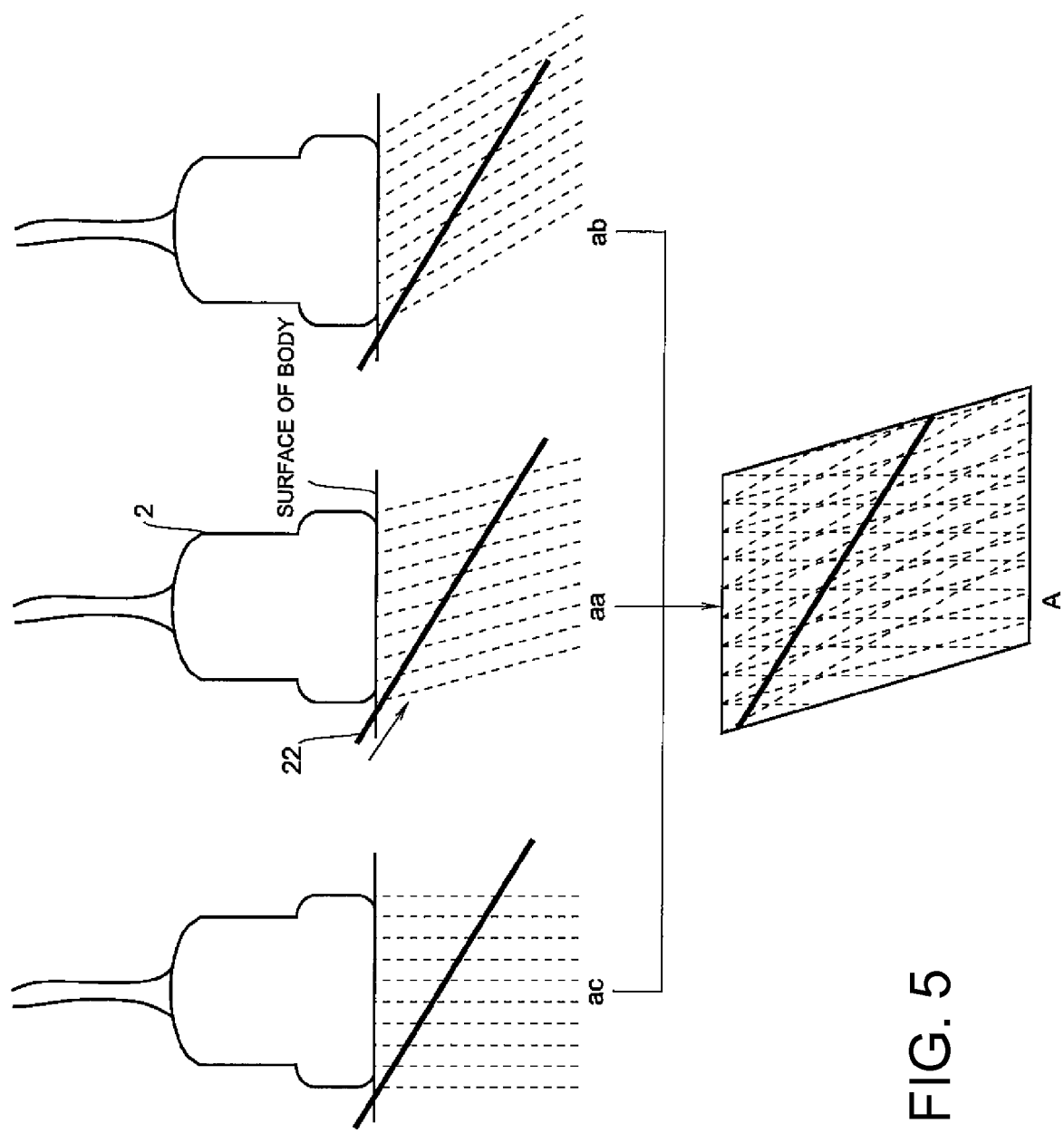
FIG. 5 is a diagram depicting a concept of a compound scan and creating a compound image.

FIG. 5 depicts a concept of FOV adjustment. FIG. 5 shows a state where a needle 22 was inserted into the body diagonally right down as indicated by an arrow. Conforming to the direction of the needle insertion, a first frame aa is scanned with acoustic lines steered rightward. Accordingly, a second frame ab is scanned with acoustic lines steered rightward relative to the direction of acoustic lines of the first frame. A third frame ac is scanned with acoustic lines steered leftward relative to the direction of acoustic lines of the first frame.

The direction of acoustic lines of the first frame aa is a reference direction of acoustic lines. The angle of the reference direction of acoustic lines can be changed optionally by the user. The direction of acoustic lines of the second frame ab and the direction of acoustic lines of the third frame ac change in relation to a change of the reference direction.

By these scans, three B-mode images are captured respectively. Capturing three B-mode images is carried out by the ultrasonic probe 2, transmitter unit 4, receiver unit 6, B-mode processing unit 8, scan converter 10, and frame buffer 12. These components are an example of a device for capturing an image in the invention. These components are also an example of capturing a right oblique image in the invention.

By aggregation of three frames aa, ab, ac, a compound image A is created. The frame of the compound image A is set to coincide with the first frame aa. The first frame aa has overlaps with the second frame and the third frame and its overlap potion is largest among these frames; therefore, it is most suitable for use as the frame of the compound image A. Hereinafter, the frame of the compound image A will simply be referred to as a frame A.

The compound image A is created by the compounding unit 14. The compounding unit 14 is an example of a device for creating an image in the invention. The compounding unit 14 is also an example of a device for creating a first compound image in the invention.

The shape of the frame A is a parallelogram with its lateral sides slanted to the right. Therefore, the frame A whose far field shifts to the right has the shape that is suitable for tracking the needle 22 inserted into the body diagonally right down within the FOV.

Consequently, the compound image A is used as a guidance image or navigation image with the FOV suitable for tracking a needle inserted into the body in the diagonally right down direction. The compound image A is displayed on the display unit 16. The display unit 16 is an example of a display device in the invention.

Figure 6:
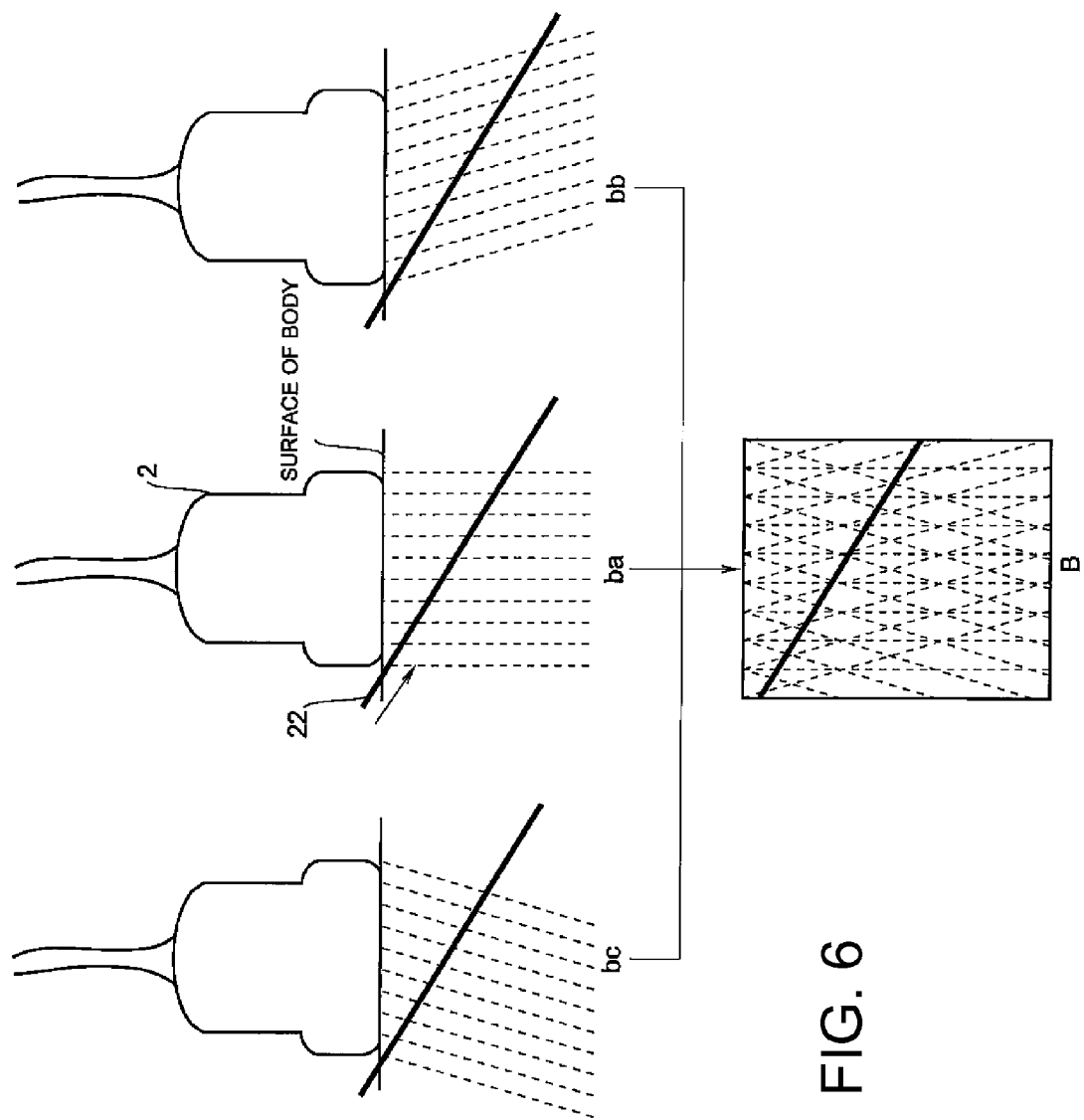
FIG. 6 is a diagram depicting a concept of a compound scan and creating a compound image.

The angle of the reference direction of acoustic lines can be changed so that the acoustic lines become square to the front, as is shown in FIG. 6. Thereby, a first frame ba is scanned with acoustic lines oriented square to the front. A second frame bb is scanned with acoustic lines steered rightward relative to the direction of acoustic lines of the first frame. A third frame bc is scanned with acoustic lines steered leftward relative to the direction of acoustic lines of the first frame.

By these scans, three B-mode images are captured respectively. Capturing three B-mode images is carried out by the ultrasonic probe 2, transmitter unit 4, receiver unit 6, B-mode processing unit 8, scan converter 10, and frame buffer 12. These components are an example of a device for capturing an image in the invention. These components are also an example of a device for capturing an image at a right angle to the front in the invention.

By aggregation of three frames ba, bb, bc, a compound image B is created. The frame of the compound image B is set to coincide with the first frame ba. The first frame ba has overlaps with the second frame and the third frame and its overlap potion is largest among these frames; therefore, it is most suitable for use as the frame of the compound image B. Hereinafter, the frame of the compound image B will simply be referred to as a frame B.

The compound image B is created by the compounding unit 14. The compounding unit 14 is an example of a device for creating an image in the invention. The compounding unit 14 is also an example of a device for creating a second compound image in the invention.

The shape of the frame B is a parallelogram with its lateral sides not slanted, namely, a rectangle. The frame B of this form is not exactly suitable for tracking the needle 22 inserted into the body diagonally right down within the FOV. However, because acoustic lines intersect with the needle 22 at angles that are nearer to right angles, the frame B can visualize the needle 22 more clearly than in the compound image A.

Consequently, the compound image B is used as a guidance image or navigation image in which the image of the needle 22 is clearer. The compound image B is displayed on the display unit 16. The display unit 16 is an example of a display device in the invention.

Figure 7:
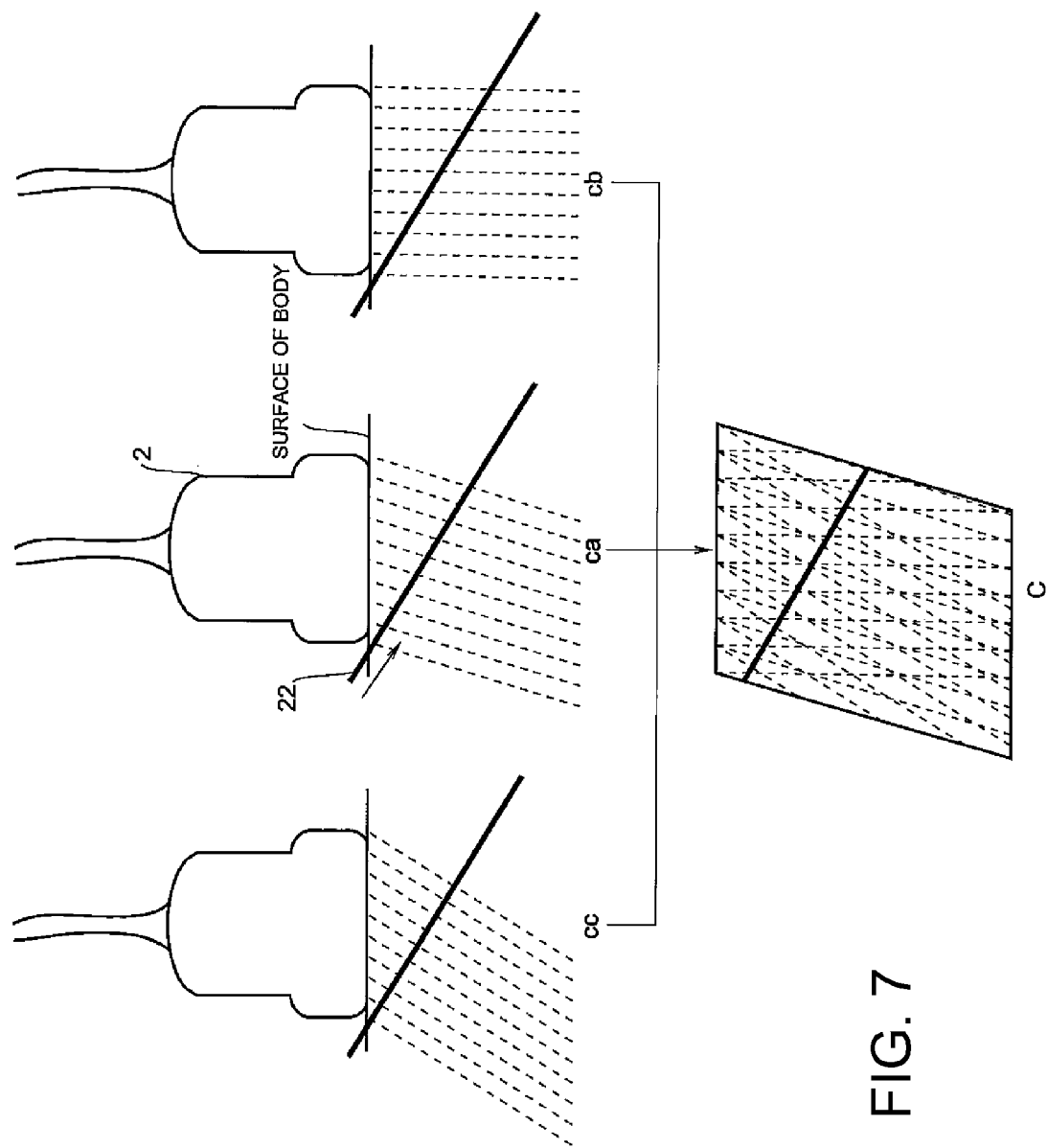
FIG. 7 is a diagram depicting a concept of a compound scan and creating a compound image.

The angle of the reference direction of acoustic lines can be changed so that the acoustic lines are steered leftward, as is shown in FIG. 7. Thereby, a first frame ca is scanned with acoustic lines steered leftward. A second frame cb is scanned with acoustic lines steered rightward relative to the direction of acoustic lines of the first frame. A third frame cc is scanned with acoustic lines steered leftward relative to the direction of acoustic lines of the first frame.

By these scans, three B-mode images are captured respectively. Capturing three B-mode images is carried out by the ultrasonic probe 2, transmitter unit 4, receiver unit 6, B-mode processing unit 8, scan converter 10, and frame buffer 12. These components are an example of a device for capturing an image in the invention. These components are also an example of a device for capturing a left oblique image in the invention.

By aggregation of three frames ca, cb, cc, a compound image C is created. The frame of the compound image C is set to coincide with the first frame ca. The first frame ca has overlaps with the second frame and the third frame and its overlap potion is largest among these frames; therefore, it is most suitable for use as the frame of the compound image C. Hereinafter, the frame of the compound image C will simply be referred to as a frame C.

The compound image C is created by the compounding unit 14. The compounding unit 14 is an example of a device for creating an image in the invention. The compounding unit 14 is also an example of a device for creating a third compound image in the invention.

The shape of the frame C is a parallelogram with its lateral sides slanted to the left. The frame C of this form is not exactly suitable for tracking the needle 22 inserted into the body diagonally right down within the FOV. However, because acoustic lines intersect with the needle 22 at nearly right angles, the frame C can visualize the needle 22 even more clearly than in the compound image B.

Consequently, the compound image C is used as a guidance image or navigation image in which the image of the needle 22 is highly clear. The compound image C is displayed on the display unit 16. The display unit 16 is an example of a display device in the invention.

Figure 8:
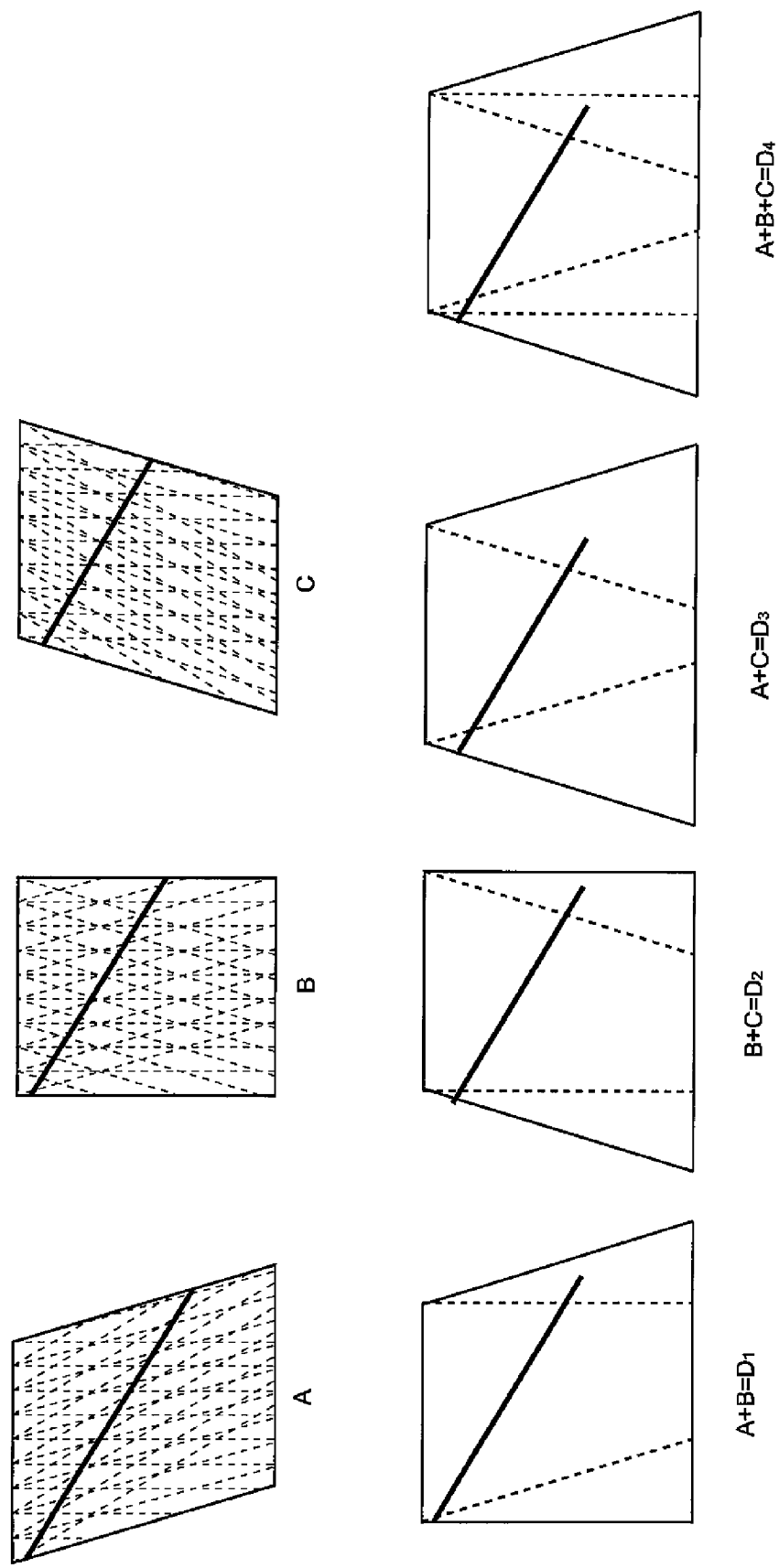
FIG. 8 is a diagram depicting a concept of creating a compound image.

The FOV of a compound image can be made more effective by combining the frames A, B, C, as appropriate. FIG. 8 depicts examples of combining the frames A, B, C. As shown in FIG. 8, a compound image D1 is created by combining the frames A and B. The frame of the compound image D1 has a form of a one-sided trapezoid in which only the right side slants. The resulting compound image D1 has both the features of the compound images A and B in terms of image quality and FOV and the width of FOV extends in the far field.

A compound image D2 is created by combining the frames B and C. The frame of the compound image D2 has a form of a one-sided trapezoid in which only the left side slants. The resulting compound image D2 has both the features of the compound images B and C in terms of image quality and FOV and the width of FOV extends in the far field.

A compound image D3 is created by combining the frames A and C. The frame of the compound image D3 has a form of a trapezoid in which both sides slant. The resulting compound image D3 has both the features of the compound images A and C in terms of image quality and FOV and the width of FOV extends in the far field.

A compound image D4 is created by combining the frames A, B, and C. The frame of the compound image D4 has a form of a trapezoid in which both sides slant. The resulting compound image D4 has all the features of the compound images A, B, and C and the width of FOV extends in the far field.

The compound images D1, D2, D3, D4 are expanded compound images. These expanded compound images are created by the compounding unit 14. The compounding unit 14 is an example of a device for creating an expanded image in the invention. These compound images D1, D2, D3, D4 are used as guidance images or navigation images that are better in both image quality and FOV.

Although an instance where the needle 22 is inserted into the body in the diagonally right down direction has been discussed above, when the needle 22 is inserted into the body in a diagonally left down direction, the compound images C, D2, D3, D4 become those having FOV that is especially suitable for tracking the needle insertion in this direction. The compound images A, B are effective for visualizing the needle 22 clearly.

FIG. 9 depicts an example of icons corresponding to the frames A, B, C, D. Each icon symbolizes each frame by a pestle-shape graphic form. Specifically, the icon a symbolizes the frame A by a pestle-shape graphic form that slants diagonally right down. The icon b symbolizes the frame B by an upright pestle-shape graphic form whose top and bottom sides are of equal length. The icon c symbolizes the frame C by a pestle-shape graphic form that slants diagonally left down. The icon d symbolizes the frame D by an upright pestle-shape graphic form whose top side is shorter than the bottom side. The icons a, b, c, d are an example of icons in the invention.

These icons are displayed with the corresponding compound image on the display unit 16 to help the user to easily recognize the type of the compound image displayed. These icons may be displayed on the display unit 16 or in a touch panel portion of the operation unit 20 and used for selection of a compound scan type.

When selection of a compound scan type is enabled using the icons, the reference direction of acoustic lines in each frame may be set to a default value which has been defined beforehand. Thereby, it is possible to simplify the way of operating the apparatus.

Many widely different embodiments of the invention may be configured without departing from the spirit and the scope of the present invention. It should be understood that the present invention is not limited to the specific embodiments described in the specification, except as defined in the appended claim.

What is claimed is:

1. An ultrasonic imaging apparatus configured to capture a plurality of B-mode images of a same cross section respectively by a plurality of linear scans with different directional ultrasonic beams and to create and display a compound image from the plurality of B-mode images, said ultrasonic imaging apparatus comprising:

an image capturing device configured to capture a plurality of B-mode images respectively by a first linear scan with an ultrasonic beam steered to a reference direction and at least a second linear scan with an ultrasonic beam steered to at least one direction different from the reference direction;

a first compound image creation device configured to create a first compound image using the plurality of B-mode images;

a second compound image creation device configured to create a second compound image using the plurality of B-mode images;

an expanded image creating device configured to create a compound image by combining the first compound image and the second compound image, wherein the image creating device is configured to create a field of view (FOV) of the compound image that coincides with a FOV of a B-mode image captured by the first linear scan; and a display device configured to display the compound image.

2. The ultrasonic imaging apparatus according to claim 1, wherein the reference direction is angled to the right.

3. The ultrasonic imaging apparatus according to claim 1, wherein the reference direction is angled to the left.

4. An ultrasonic imaging apparatus configured to capture a plurality of B-mode images of a same cross section by a plurality of linear scans with different directional ultrasonic beams respectively and to create and display a compound image from the plurality of B-mode images, said ultrasonic imaging apparatus comprising:

a right oblique image capture device configured to capture a plurality of B-mode images respectively by a first linear scan with an ultrasonic beam oriented at a first reference direction that is angled to the right and a first subsequent linear scan with an ultrasonic beam steered to a direction different from the first reference direction;

a right angle image capture device configured to capture a plurality of B-mode images respectively by a second linear scan with an ultrasonic beam oriented at a second reference direction that is square to the front and a second subsequent linear scan with an ultrasonic beam steered to a direction different from the second reference direction;

a left oblique image capture device configured to capture a plurality of B-mode images respectively by a third linear scan with an ultrasonic beam oriented at a third reference direction that is angled to the left and a third subsequent linear scan with an ultrasonic beam steered to a direction different from the third reference direction;

a first compound image creation device configured to create a first compound image using the plurality of B-mode images captured by said right oblique image capture device;

a second compound image creation device configured to create a second compound image using the plurality of B-mode images captured by said right angle image capture device;

a third compound image creation device configured to create a third compound image using the plurality of B-mode images captured by said left oblique image capture device;

an expanded image creation device configured to create an expanded compound image by combining at least two of the first compound image, the second compound image, and the third compound image; and a display device configured to display the expanded compound image.

5. The ultrasonic imaging apparatus according to claim 4, wherein:

a field of view (FOV) of the first compound image coincides with a FOV of a B-mode image captured by the first linear scan;

a FOV of the second compound image coincides with a FOV of a B-mode image captured by the second linear scan;

a FOV of the third compound image coincides with a FOV of a B-mode image captured by the third linear scan; and a FOV of the expanded compound image coincides with a FOV that includes at least two of the FOV of the first compound image, the FOV of the second compound image, and the FOV of the third compound image.

6. The ultrasonic imaging apparatus according to claim 1, wherein the reference direction is variably angled.

7. The ultrasonic imaging apparatus according to claim 4, wherein the reference direction is variably angled.

8. The ultrasonic imaging apparatus according to claim 1, wherein the at least a second linear scan includes a two linear scans, each linear scan with an ultrasonic beam steered in a separate direction different from the reference direction.

9. The ultrasonic imaging apparatus according to claim 4, wherein at least one of the first subsequent linear scan, the second subsequent linear scan, and the third subsequent linear scan includes two linear scans, each linear scan with an ultrasonic beam steered in a separate direction different from a corresponding reference direction.

10. The ultrasonic imaging apparatus according to claim 8, wherein the two directions are one direction steered rightward and the other direction steered leftward relative to the reference direction.

11. The ultrasonic imaging apparatus according to claim 1, wherein said display device is configured to display an icon for each FOV.

12. The ultrasonic imaging apparatus according to claim 5, wherein said display device is configured to display an icon for each FOV.

13. An ultrasonic imaging method comprising:

capturing a plurality of B-mode images of a same cross section respectively by a first linear scan with an ultrasonic beam steered to a reference direction and at least a second linear scan with an ultrasonic beam steered to a direction different from the reference direction;

creating a first compound image using the plurality of B-mode images;

creating a second compound image using the plurality of B-mode images;

creating an expanded compound image by combining the first compound image and the second compound image, wherein a field of view (FOV) of the compound image coincides with a FOV of a B-mode image captured by the first linear scan; and displaying the compound image.

14. The ultrasonic imaging method according to claim 13, wherein the reference direction is angled to the right.

15. The ultrasonic imaging method according to claim 13, wherein the reference direction is angled to the left.

16. The ultrasonic imaging method according to claim 13, wherein the reference direction is variably angled.

17. The ultrasonic imaging method according to claim 13, wherein the at least second linear scan includes two linear scans, each linear scan with an ultrasonic beam steered in a separate direction different from the reference direction.

18. The ultrasonic imaging method according to claim 13, wherein displaying the compound image comprises displaying an icon for each FOV.

* * * * *